(12) United States Patent
Stoy et al.

(10) Patent No.: US 12,357,800 B2
(45) Date of Patent: Jul. 15, 2025

(54) COMBINED OSMOTIC AND HYDROGEL CERVICAL DILATORS AND METHOD OF MAKING SAME

(71) Applicant: MEDICEM TECHNOLOGY S.R.O., Kamenne Zehrovice (CZ)

(72) Inventors: Vladimír Stoy, Tuchomerice (CZ); Tomas Drunecký, Kysice (CZ); Miroslav Dudic, Praha 4 Krc (CZ); Petr Stehlicek, Kladno (CZ); Zdenka Vokounova, Rudna (CZ)

(73) Assignee: MEDICEM TECHNOLOGY S.R.O., Kamenne Zehrovice (CZ)

( * ) Notice: Subject to any disclaimer, the term of this patent is extended or adjusted under 35 U.S.C. 154(b) by 0 days.

(21) Appl. No.: 18/323,934

(22) Filed: May 25, 2023

(65) Prior Publication Data
US 2023/0293865 A1    Sep. 21, 2023

Related U.S. Application Data

(63) Continuation of application No. 16/339,977, filed as application No. PCT/IB2017/056187 on Oct. 6, 2017, now Pat. No. 11,660,431.
(Continued)

(51) Int. Cl.
*A61M 29/02* (2006.01)
*A61B 17/00* (2006.01)
(Continued)

(52) U.S. Cl.
CPC .............. *A61M 29/02* (2013.01); *A61B 17/00* (2013.01); *A61L 31/145* (2013.01);
(Continued)

(58) Field of Classification Search
CPC .......... A61M 29/02; A61M 2205/0216; A61M 2207/00; A61M 2210/1433; A61B 17/00;
(Continued)

(56) References Cited

U.S. PATENT DOCUMENTS 4,480,642 A * 11/1984 Stoy ............... A61M 29/02
606/119
5,085,807 A    2/1992 Okamoto et al.
(Continued)

FOREIGN PATENT DOCUMENTS

WO      84/00494 A1    2/1984
WO      95/03848 A1    2/1995
(Continued)

*Primary Examiner* — Richard G Louis
(74) *Attorney, Agent, or Firm* — Fox Rothschild LLP

(57) ABSTRACT

A cervical dilator including a stem comprising a partly or fully dehydrated hydrogel comprising a water-insoluble synthetic hydrophilic polymer capable of radial expansion due to absorption of water from a bodily fluid. The cervical dilator softens and ripens the cervical tissue and expands the cervical canal by a combined action of radial hydrogel stem expansion and osmotic withdrawal of water from the tissue. The osmotic withdrawal is caused by at least one osmotically active compound, such as a water-soluble salt, a polyelectrolyte, or a mixture thereof, wherein the at least one osmotically active compound is dispersed in the hydrogel. The cervical dilator may also include a non-toxic plasticizer of the hydrogel, such as water.

17 Claims, 2 Drawing Sheets

TOP: DEHYDRATED STATE,
BOTTOM: HYDRATED STATE

Related U.S. Application Data

(60) Provisional application No. 62/404,997, filed on Oct. 6, 2016.

(51) Int. Cl.
*A61L 31/14* (2006.01)
*A61B 17/42* (2006.01)

(52) U.S. Cl.
CPC .............. *A61B 2017/00893* (2013.01); *A61B 2017/00898* (2013.01); *A61B 2017/00942* (2013.01); *A61B 2017/4225* (2013.01)

(58) Field of Classification Search
CPC .......... A61B 2017/00893; A61B 2017/00898; A61B 2017/00942; A61B 2017/4225; A61B 2034/301; A61B 17/42; A61B 90/02; A61B 2017/4216; A61L 31/145; A61L 31/14; A61P 15/00; B29C 37/0092; B29C 55/005
See application file for complete search history.

(56) References Cited

U.S. PATENT DOCUMENTS

| | | | | |
|---|---|---|---|---|
| 5,525,356 | A | * | 6/1996 | Jevne ................... A61N 1/0428 424/484 |
| 2001/0046518 | A1 | | 11/2001 | Sawhney |
| 2002/0068180 | A1 | * | 6/2002 | Yang ..................... A61L 29/085 428/447 |
| 2003/0100830 | A1 | | 5/2003 | Zhong et al. |
| 2003/0212416 | A1 | * | 11/2003 | Cinelli .................. A61K 8/042 606/134 |
| 2004/0143180 | A1 | * | 7/2004 | Zhong .................. G01R 33/286 623/1.34 |
| 2009/0012486 | A1 | * | 1/2009 | Riegel .................... A61L 15/60 427/213 |
| 2009/0024107 | A1 | * | 1/2009 | Wilson ................... A61F 2/442 604/509 |
| 2014/0296418 | A1 | | 10/2014 | Sato et al. |

FOREIGN PATENT DOCUMENTS

| | | |
|---|---|---|
| WO | 01/022902 A2 | 4/2001 |
| WO | 03/037161 A2 | 5/2003 |
| WO | 2004/073690 A1 | 9/2004 |

\* cited by examiner

COMBINED OSMOTIC AND HYDROGEL CERVICAL DILATORS AND METHOD OF MAKING SAME

CROSS-REFERENCE TO RELATED APPLICATIONS

This application is a continuation of U.S. application Ser. No. 16/339,977, filed Apr. 5, 2019, issuing May 30, 2023 as U.S. Pat. No. 11,660,431, which is a 371 of PCT/IB2017/056187, filed Oct. 6, 2017, which claims the benefit of priority to U.S. Provisional Patent Application No. 62/404,997, filed Oct. 6, 2016. The disclosure of each is incorporated herein by reference in its entirety.

FIELD OF THE INVENTION

The present invention relates to cervical dilators, and methods of manufacturing cervical dilators.

BACKGROUND OF THE INVENTION

Tissue expansion is used in a variety of surgical procedures. The tissue expansion can be either temporary or permanent. One well-known example of temporary expansion is dilatation of the cervical canal in gynecology. It is achieved naturally during childbirth, but it can also be achieved artificially by various means, such as by administration of prostaglandins (see M J Keirse, *Prostaglandins in preinduction cervical ripening. Meta-analysis of worldwide clinical experience*, The Journal of reproductive medicine (1993) 38: 89-100). The cervical canal can also be temporarily expanded in response to a short-term radial stress using a mechanical dilator. Mechanical dilators are usually sets of plastic or metal rods of various designs (e.g., Hegar dilators, Hank dilators) of increasing diameter that are forced sequentially into the cervical canal. Newer mechanical dilators are described, for example, in U.S. Pat. No. 7,105,007 (entitled Cervical medical device, system and method). The mechanical pressure generated by these devices partly and reversibly dehydrates the tissue that thus becomes softer and more deformable. However, the maximum rate of the partial dehydration generated by the mechanical pressure is controlled by hydraulic permeability of cell walls, and draining of water from the tissue takes some time. Consequently, mechanical dilators force tissue to expand faster than the dehydration rate allows, and this may cause rupture of cell membranes and consequent tissue damage, even scarring.

Therefore, inflatable dilating catheters of various designs were developed (see e.g., US Patent Publication US 2004/0116955 and U.S. Pat. No. 4,664,114) allowing for a somewhat safer, slower and more controllable cervical dilatation. However, the dilatation rate is still not controlled easily, and thus may easily exceed the safe limit derived from the drainage rate of bodily fluids from the tissue.

An alternative to the mechanical dehydration of cervical tissue is osmotic dehydration utilizing drainage of water from the tissue in response to a local osmotic non-equilibrium. This method is utilized by Lamicel® osmotic dilators that dehydrate cervical tissue by using magnesium sulfate salt dispersed in pores of a synthetic sponge carrier (see U.S. Pat. No. 4,467,806). Such tissue softening and dilation is reversible with minimum changes in hormonal levels or permanent changes of the cervical tissue. These devices work on purely osmotic principle since the hydrogel sponge used as the salt carrier is inherently soft and cannot generate any significant mechanical pressure against the tissue.

Even more effective are osmotic hydrogel cervical dilators combining local osmotic tissue dehydration with mechanical expansion due to the device swelling. This method employs insertion of a dehydrated hydrogel (or "xerogel") stem into the cervical canal. The xerogel is hypertonic with respect to the contacting tissue and thus draws water from the tissue. The osmotic gradient gradually decreases as the osmolarity increases in the tissue and decreases in the hydrogel stem, until the equilibrium is reached. The stem expands in its volume as the xerogel hydrates to become the hydrogel. This expansion generates a controlled mechanical pressure against the cervical tissue assisting in its dehydration. In addition, this expansion helps to maintain an intimate contact between the tissue and the device that is needed for osmotic transport of water. Consequently, a hydrogel cervical dilator combines the mode of the mechanical dilators and osmotic dilators for an optimum result.

Hydrogels have been used for tissue expansion for some time. For a "natural" means of cervical expansion, dried stems of seaweed *Laminaria Japonica* ("LJ") have been used for cervical expansion for centuries (see e.g., U.S. Pat. No. 4,624,258, and M H Goldrath, Vaginal removal of the pedunculated submucous myoma: the use of laminaria, Obstetrics and gynecology (1987) 70: 670-2). The stem of LJ contains a natural polysaccharide hydrogel capable of expanding the dried stem upon its rehydration generating both osmotic transport of water and mechanical expansion during the hydration by water from bodily fluids. However, dilators from LJ have various disadvantages: the hydration is relatively slow and rather irregular, the shape and geometry of the dried stems is rather irregular, osmotic pressure is relatively low, mechanical expansion against the pressure of stiff cervical tissue (e.g., in the internal os) may be limited, the mechanical strength in the state of maximum hydration may be too low to prevent disintegration, sterilization of the product may be uncertain and there is no design feature or property that would prevent multiple use and thus decrease the risk of infection.

These shortcomings have led to a search for improved synthetic hydrogel dilators. For example, a compound hydrogel dilator was proposed by A. Michaels in U.S. Pat. No. 4,237,893, while V. Stoy et al. employed synthetic acrylic hydrogels for anisotropically swelling synthetic hydrogel dilators in U.S. Pat. No. 4,480,642. As such, products such as DILAPAN S® cervical expanders, for example, can now replace both dried LJ stems and osmotic Lamicel® dilators (see e.g., D A Grimes et al., *Lamicel versus laminaria for cervical dilation before early second-trimester abortion: a randomized clinical trial*, Obstetrics and gynecology (1987) 69: 887-90; and EC Wells et al., *Cervical dilation: A comparison of Lamicel and Dilapan*, American journal of obstetrics and gynecology (1989) 161: 1124-6).

SUMMARY OF THE DISCLOSURE

The invention is directed to a cervical dilator including a stem comprising a partly or fully dehydrated hydrogel comprising a water-insoluble synthetic hydrophilic polymer capable of radial expansion due to absorption of water from a bodily fluid. The cervical dilator further includes at least one osmotically active compound dispersed within the hydrogel.

In addition, a method of manufacturing this cervical dilator is described herein. The method includes providing a hydrogel in a partly or fully dehydrated state, and axially stretching the hydrogel at a temperature above the glass transition temperature of the water-insoluble synthetic hydrophilic polymer, thereby producing the stem comprising the partly or fully dehydrated hydrogel, and achieving the capability of radial expansion. Then, the stem comprising the partly or fully dehydrated hydrogel is subsequently cooled under the axial stress to an ambient temperature.

Furthermore, an additional method of manufacturing this cervical dilator is described herein. The method includes providing a hydrogel in a hydrated state, and axially stretching the hydrogel and maintaining a predetermined length of the hydrogel while drying the hydrogel, thereby producing the stem comprising the partly or fully dehydrated hydrogel, and achieving the capability of radial expansion.

DETAILED DESCRIPTION

Figure 1:
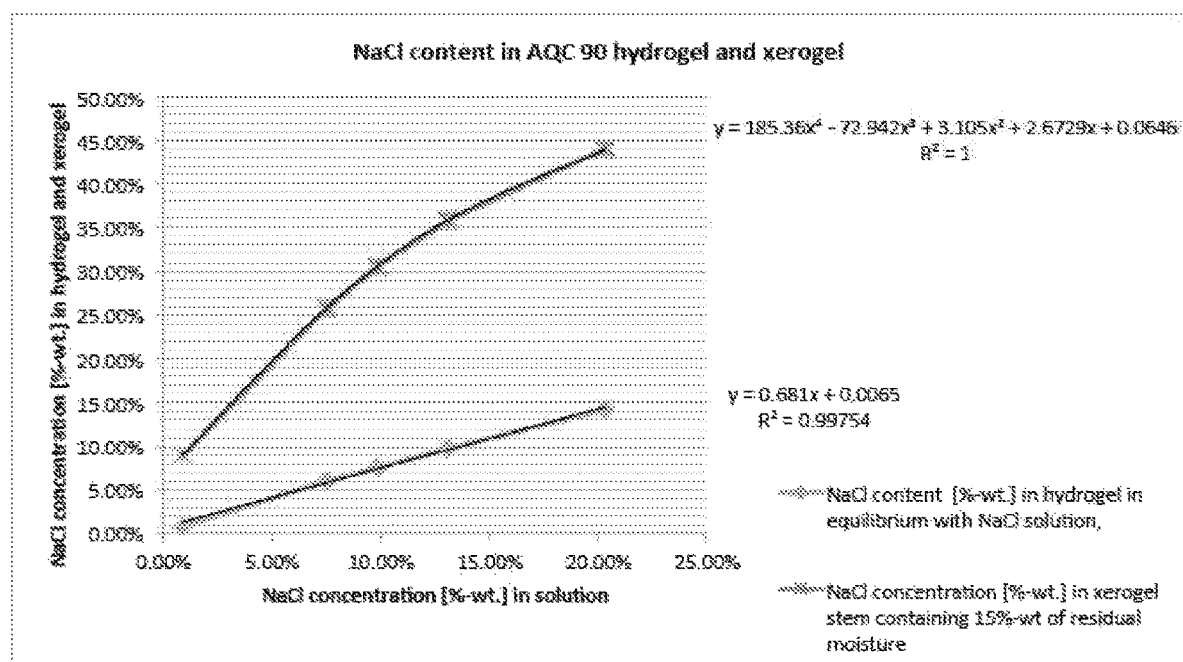
FIG. 1 shows a graph of the concentration of NaCl in the hydrogel in equilibrium with the NaCl solution and in the final xerogel stem in accordance with Example 1.

The present invention allows for a more effective hydrogel cervical dilator by dispersing at least one osmotically active compound within a partly or fully dehydrated synthetic hydrogel stem, thus combining more than one means of osmotic dehydration of cervical tissue into one device. The osmotically active compound is an ionic water-soluble substance capable of absorbing water and—if not embedded within the hydrogel—forming an aqueous solution. The osmotically active compound is dispersed in the hydrogel material (i.e., hydrogel matrix) of the stem.

In one embodiment of the cervical dilator, a low-molecular weight or polymeric salt is dispersed in an anisotropically expanding dehydrated hydrogel. While both salts and dehydrated hydrogels can be used to generate an osmotic gradient to withdraw some water from the surrounding tissue, there are some differences between the two. Specifically, the osmotic pressure and volume of the water drawn from the tissue will be higher for a salt than for a correspondingly partly dehydrated hydrogel (xerogel). As used herein, the term "xerogel" refers to a hydrogel dehydrated to its hard state, i.e., to the state with residual water concentration at which the glass transition temperature ($T_g$) is higher than ambient or body temperature, whichever is higher. As used herein, the term "partly dehydrated hydrogel" refers to a hydrogel in its plasticized (i.e., reversibly deformable) or rubbery (i.e., elastic) state in which the water content is sufficient to decrease the $T_g$ below ambient temperature, but is lower than the liquid content in equilibrium with an isotonic aqueous solution. As these terms refer to a hydrogel component having differing levels of dehydration, unless there is a particular reason noted to distinguish between "xerogel" and "partly dehydrated hydrogel," these two terms are used interchangeably herein. In addition, although salts may migrate away from the dilation site by diffusion or by flowing away when dissolved, hydrogels, on the other hand, stay in place until removed. Also, salts cannot generate a mechanical pressure against the cervical tissue, as hydrogels do. Finally, some multivalent ions from the salts (e.g., $Ca^{2+}$, $Al^{3+}$, $Zn^{2+}$ or $Mg^{2+}$) may generate high osmotic pressure, but can also interact with tissue components (e.g., proteins) and cause an adverse reaction. In contrast, hydrogels are generally inert with respect to the tissue components and highly biocompatible.

In another embodiment of the cervical dilator, the at least one osmotically active compound is a polyelectrolyte, preferably a polyelectrolyte salt with a fixed negative charge containing negatively charged pendant units, such as for example, carboxylate units, sulphate units, sulfonic acid units or phosphate units. Examples of such polyelectrolytes are polymers and copolymers of acrylic and methacrylic acid; poly(ethylene sulfonic acid); poly(phosphoric acid); poly(styrene sulfonic acid); poly(vinyl sulfuric acid); poly (vinylphosphonic acid); poly(maleic acid); poly(2-methacryloyloxyethane-1-sulfonic acid); poly(3-methacryloyloxypropane-1-sulfonic acid); poly(3-(vinyloxy)propane-1-sulfonic acid); poly(4-vinylphenyl sulfuric acid); and their respective salts, particularly salts with monovalent counter-cations such as sodium, potassium, lithium, ammonium or organic bases such as $NR_4^+$ or $NR_3H^+$ (wherein R denotes alkyl or hydroxyalkyl substituents with one to four carbon atoms), pyridine, etc. We note that many of the organic bases are biologically active and can also serve to suppress pain, infections, etc. In addition, the water-soluble polyelectrolytes useful as the osmotically active compound can also be formed by other water soluble ionic polymers and copolymers well known to those of ordinary skill in the art.

Advantageously, the polyelectrolyte is entrapped in the hydrogel network. Preferably, at least 50%-wt., and more preferably at least 90%-wt. of the entrapped polyelectrolyte remains entrapped within the hydrogel during the course of the cervical expansion procedure. The polyelectrolyte may be formed within the hydrogel network, for example, by polymerization of the polyelectrolyte-forming water-soluble monomer within the hydrogel network. This method leads to one type of an interpenetrating network. Conversely, the hydrogel network may be formed around polyelectrolyte chains or particles by polymerization of monomer molecules, or by coagulation of the hydrogel-forming chains in the presence of the polyelectrolyte, or by other techniques of polymer formation known to those of ordinary skill in the art. This leads to a different type of the interpenetrating network, or to a structure with discrete osmotic cells dispersed within the continuous hydrogel material.

Preferably, the polyelectrolyte is present in the cervical dilator in a concentration from about 1%-wt. to about 60%-wt., more preferably from about 1%-wt. to about 50%-wt., even more preferably from about 5%-wt. to about 40%-wt., and still more preferably from about 5%-wt. to about 20%-wt., based on the weight of the dehydrated hydrogel stem.

The polyelectrolyte may be advantageously combined with positively charged monovalent counter-cations, such as $Na^+$, $K^+$, $Li^+$, $NH_4^+$, $NR_4^+$ or $NR_3^+$ (wherein R denotes alkyl or hydroxyalkyl substituents with one to four carbon atoms) or a mixture thereof, to form another embodiment of the osmotically active compound.

In another embodiment of the cervical dilator, at least one of the osmotically active compounds is a low-molecular weight, non-toxic water-soluble salt capable of diffusing out of the hydrogel at least in its fully hydrated state, and formed by a combination of a monovalent cation and a mono-, di-, tri- or even multivalent anion. Preferably, the monovalent cation is $Na^+$, $K^+$, $Li^+$, $NH_4^+$, $NR_4^+$ or $NR_3H^+$ (wherein R denotes alkyl or hydroxyalkyl substituents with one to four carbon atoms), or any mixture thereof.

In another embodiment, these monovalent cations are combined with water-soluble negatively charged counterions such as, for example, $Cl^-$, $F^-$, $Br^-$, $SO_4^{2-}$, $CNS^-$, $PO_3^{3-}$, $PO_3H^{2-}$, $PO_3H^{2-}$, $CO_2^{2-}$, $CO_2H^-$, $HCOO^-$, $CH_3COO^-$, $HO(CH_2)_nCOO^-$ (wherein n is an integer from 1 to 6), or anions derived from organic hydroxyl-acids or amino acids, or a combination thereof. One of the preferred salts is sodium chloride because of its natural presence in bodily fluids and its solubility, which is relatively independent of temperature.

The cation-anion combination may be dispersed within the hydrogel in the form of a solid substance salt, in the form of a highly concentrated aqueous salt solution or in a combination thereof. For example, the salts can be uniformly dispersed in a continuous hydrogel matrix, or they may form a concentration gradient where more salt is located on the hydrogel surface than is located within its bulk. In one embodiment, the salt may form crystals fully or partially embedded in the dehydrated hydrogel matrix. Preferably, the hydrogel forms a continuous polymer matrix rather than a sponge that could not generate a significant external pressure due to its expansion.

Preferably, the salt is incorporated into the hydrogel in two basic steps. First, the hydrogel is contacted with an excess of the aqueous solution of the selected salt and the salt ions (cations and anions) are allowed to diffuse into the hydrogel. The salt concentration within the hydrogel gradually approaches the equilibrium value when the ratio of concentrations within and outside of the hydrogel corresponds to the respective partition coefficient. The diffusion of the ions into the hydrogel can be accelerated by increased temperature.

Next, after a predetermined amount of time or when the concentration of ions reaches a predetermined value based on the desired final salt concentration, then the hydrogel is removed from the aqueous solution and placed on suitable drying racks. The hydrogel is stretched by a predetermined ratio that is calculated to achieve the desired axial and radial change of dimensions between the dehydrated state and the hydrated state of the hydrogel. It has been established that the dehydrated hydrogel stem should not change its length preferably by more than about one quarter (+ or −25%) in either direction by maximum swelling in physiological conditions. Even more preferably, the axial change by hydration of the stem length should be from minus 20% to plus 10%. The axial length change can be controlled by the hydration and by the degree of stretching at the beginning of this drying step. If the hydrogel is stretched more prior to the drying, then it expands less, or even shrinks due to the hydration.

For example, the stretching ratio can be determined as follows. First, the Volume Expansion Factor, or VEXF can be calculated. The VEXF is the ratio of volume in the final hydrogel state 1 to the volume in the initial xerogel state 0. It is understood that the states 1 and 0 may be in vivo or in vitro while the needed parameters are determined in simulated experimental conditions.

In the state 0, starting with a xerogel of mass $G_0$ composed of $g_{10}$ grams of solvent, water-soluble salt or plasticizer (including residual water) and $g_{20}$ grams of polymer, then the weight fraction of solvent will be $w_{10}=g_{10}/G_0$, a weight fraction of polymer will be $w_{20}=g_{20}/G_0$, and $w_{10}+w_{20}=1$. With the density of the polymer being $d_p$ and density of the solvent be $d_s$, and assuming that fractional volumes of the polymer and the solvent will be additive (i.e., approximating the mix as "an ideal solution"), then the density of the expander in its initial state will be $d_{e0}=d_{10}*(1-w_{20})+d_{20}*w_{20}$ and its volume will be $V_0=G_0/d_{e0}$.

In the state 1, the hydrogel weight reaches $G_1$ as the solvent is exchanged for the external isotonic medium that swells the polymer. The dilator now consists of the same amount of polymer $g_{20}$ (the natural assumption is that the polymer is insoluble in the isotonic medium), but of a different amount of the isotonic medium $g_{m1}$. Hence, $G_1=g_{20}+g_{m1}$, and weight fractions of the isotonic medium and polymer are $w_{m1}=g_{m1}/G_1$ and $w_{21}=g_{20}/G_1$, respectively, while $w_{m1}+w_{21}=1$. The density of the expander in the state 1 will be $d_{e1}=d_{m1}*(1-w_{21})+d_{20}*w_{21}$, under the same assumption that fractional volumes will be additive as was used in the initial state. The volume of the expander will now be $V_1=G_1/d_{e1}$ and $VEXF=V_1/V_0$.

One can also observe that the volume fractions of polymer $v_{20}=(g_{20}*d_{20})/(G_0*d_{e0})$ and $v_{21}=(g_{20}*d_{20})/(G_1*d_{e1})$, such that $v_{20}*G_0*d_{e0}=v_{21}*G_1*d_{e1}$ and hence $v_{20}*V_0=v_{21}*V_1$ so that $VEXF=v_{20}/v_{21}$.

In other words, the volume expansion factor (VEXF) of a hydrogel between two different states with two different liquid contents is equal to the reciprocal ratio of volume fraction of polymer in these two states. Alternatively, VEXF can be calculated from the relative weight change as $VEXF=(G_1/G_0)*(d_{e1}/d_{e0})$.

Knowing the VEXF value for a given xerogel-hydrogel system, one can calculate the Linear Expansion Factor, or LINEXF, in three different directions. In the case of isotropic change, $LINEXF=VEXF^{\wedge(1/3)}$. For anisotropic swelling, linear expansion factors have to be defined for three separate dimensions, e.g., $LINEXF_x$, $LINEXF_y$ and $LINEXF_z$, and it then holds that $VEXF=LINEXF_x*LINEXF_y*LINEXF_z$.

As an example, let us consider a cylindrical xerogel stem from a multi-block acrylic copolymer capable of the final VEXF=8 and wherein the three-fold increase of diameter (for instance, from about 4 mm+/−0.2 mm in the xerogel state to about 12 mm in the fully hydrated state) is required. If the xerogel swells isotropically, then $LINEXF=VEXF^{\wedge(1/3)}=2$ in each direction and the final diameter would be only 8 mm. At the same time, the length of the stem would also increase by a factor of two, e.g., from 65 mm to 130 mm. To achieve the required diameter of 12 mm by isotropic expansion, the length would have to increase to 195 mm-which is too much from the viewpoint of the anatomy of the cervix. And the VEXF would have to have a value of 27, i.e., to grow 27 times in volume, so that the final hydrogel would contain a very low concentration of the polymer. This would result in very low mechanical strength and very low swelling pressure against the cervical tissue.

Now, if we start with the hydrogel rod in its final hydrated state and with the final desired dimensions (for instance, a hydrated diameter of 12 mm and hydrated length of 55 mm), and considering the length in the Z-axis direction, then $LINEXF_zx=55/65=0.85$. This can be achieved if the hydrogel is stretched $(LINEXF_z)^{\wedge(-1)}=1.18$ times in length and fixed at this length until it dries to the xerogel state. The diameter decrease from the hydrogel to the xerogel state will be by a factor of $1/LINEXF_d=1/((VEXF/LINEXF_z)^{\wedge(1/2)})=1/(8*1.18)^{\wedge}2=0.325$. Therefore, the xerogel stem will have a diameter of 3.9 mm and a length of 65 mm, and will change its dimensions to the required diameter of 12 mm and length of 55 mm in the fully hydrated state.

The stretched hydrogel rods can be dried to the predetermined water content. A predetermined amount of water is removed by evaporation while the hydrogel is subject to axial tension. The drying with the fixed length generates stress that orients polymer chains in a preferential axial direction. And as the hydrogel rehydrates via the water from bodily fluids, randomization of the oriented chains decreases axial expansion and increases radial expansion, which is advantageous for the cervical canal expansion.

Air-drying in the axially stressed state can be carried out under various conditions (temperature, airflow, air humidity, etc.) leading to a smooth surface and a uniform xerogel rod diameter. The optimum drying conditions are related to the desired drying time, desired xerogel surface quality and acceptable variability of the xerogel stem diameter. In one embodiment, the preferred drying process is performed first in ambient temperature in air of relative humidity lower than 50% until more than 50% by weight of the water is removed, and then the drying is finished at an elevated temperature above 70° C. while the stem rods are still fixed on the drying rack. Another drying method uses high drying temperature above about 105° C. at which even fully dehydrated polymer is in its rubbery state.

Generally speaking, the conditions of drying are selected in such a way that water evaporated from the surface can be replaced by diffusion from the interior to the extent sufficient to keep the outer skin in the partly hydrated and deformable state. If the evaporation is too fast and/or the temperature is too low, then the outer surface may form a deformed "skin."

The resulting xerogel rod contains the preset concentration of salts that depends upon parameters such as the diffusion time, diffusion rate, partition coefficient, hydration of the polymer at a given salt concentration, etc., which would be well understood by one of ordinary skill in the art. For example, the xerogel may contain from about 3%-wt. to 50%-wt. of the salt or of a mixture of different salts. Higher salt concentrations provide for higher osmotic dehydration, but are generally more difficult to achieve because of the limited solubility of certain salts and due to the osmotic dehydration of the hydrogel. Thus, it is preferable if the salt concentration ranges from 7%-wt. to 25%-wt., and even more preferable if the salt concentration range from 9%-wt. to 19%-wt., based on the xerogel mass.

Various distributions of the salt concentration within the xerogel can be achieved by varying the salt concentration and drying conditions. For example, one of the embodiments included conditions leading to an increase of the salt concentration from the center of the xerogel toward the periphery, with the salt being present on the xerogel surface in the form of fine crystals embedded into the surface layer of the xerogel. Such a salt distribution can cause faster tissue dehydration and improved cervix ripening and expansion. The salt distribution is controlled by its concentration and by the drying process conditions. Higher salt concentrations (for example, typically above 10% to 15% by weight, depending on the salt type and hydrogel composition) generate steeper concentration gradients, or even a "skin" of fine salt crystals embedded into the xerogel. Slower drying regimens (lower drying temperatures, higher relative humidity of the drying air) tend to further support this salt separation and formation of larger salt crystals. Preferably, the salt concentration in the xerogel is 5% to 15% by weight, although salt concentrations up to 50% by weight can be achieved and employed.

In another embodiment of the cervical dilator, the hydrogel in the dilator is plasticized by a suitable non-toxic, polar liquid capable of depressing the glass transition temperature of the water-insoluble synthetic hydrophilic polymer forming the hydrogel. Such a plasticizer will make the xerogel less brittle and prone to fracturing, particularly at lower temperatures. In addition, it will accelerate the diffusion of water into the hydrogel, thus increasing swelling of the amorphous phase in the hydrogel. The plasticized xerogel will be more deformable such that it can be more easily bent or formed to fit a particular geometry of a cervical canal. And lastly, it can make the xerogel stem softer, which will decrease the risk of tissue damage during insertion. The most preferred plasticizers are glycerol, glycerol monoacetate, glycerol diacetate, glycerol formate, glycolic acid, 1,2 propylene glycol, dimethyl sulfoxide (DMSO), water, or any mixtures thereof.

Preferably, the plasticizer is present in a concentration ranging from about 3%-wt. to 25%-wt., based on the weight of the xerogel. More preferably, the plasticizer is water present in a concentration ranging from about 5%-wt. to 22%-wt., based on the weight of the xerogel. A particularly preferred plasticizer is water that can be absorbed into the sterile xerogel through a semipermeable membrane, such as a permeable sterilization pouch designed for autoclaving or gas sterilization. Once the desirable concentration of water in the xerogel is reached, the device can be sealed into a secondary pouch impermeable for water or water vapors.

Another advantage of water as a plasticizer is its facilitating of the xerogel sterilization by ionizing radiation, such as gamma or beta radiation. In particular, sterilization in the presence of an aqueous plasticizer decreases discoloration of the xerogel and improves mechanical properties of the hydrogel after its full hydration. The recommended irradiation doses for sterilization by gamma or beta radiation are from 20 kGy to 50 kGy, and preferably from 25 kGy to 45 kGy.

One aspect of the cervical dilator disclosed herein is the anisotropic swelling from the partly to fully dehydrated xerogel to the hydrogel that is hydrated by the water absorbed from tissue and bodily fluids. For example, the xerogel stem can expand radially to at least double, and to even at least triple its original diameter, while its axial expansion is much smaller and can even be negative (i.e., the stem shrinks in length). In practice, the axial change should be less than one quarter of the original length (i.e., + or −25%) of the xerogel stem. The anisotropicity of the stem expansion is important for the cervix dilation. For example, if the requirement is a radial expansion from 4 mm diameter to 12 mm diameter, then an isotropic expansion would increase the stem length from the original, for example, 65 mm to the excessive length of 195 mm. More importantly, the three-fold expansion equal in all directions would translate into a 27-fold increase in the stem volume. That would leave the hydrogel with a very small volume fraction of the polymer component (approximately 3.7%-vol. if the original xerogel would contain the polymer only). Such a small concentration of a polymer network would not likely provide sufficient mechanical strength or a sufficient swelling pressure.

The cervical dilator disclosed herein also includes a stem comprising a partly or fully dehydrated hydrogel. The mechanical and physical-chemical properties of the hydrogel are important for the functioning of the cervical dilator. For example, the physical-chemical properties include maximum hydration rate (expressed, e.g., as the equilibrium liquid content) and swelling pressure generated at a particular hydration rate, while the mechanical properties in the fully hydrated state include tensile strength, relative extension at break and resistance to fracture propagation. Preferably, the hydration rate of the hydrogel corresponds to a liquid content between 75%-wt. and 95%-wt. in the equilibrium against isotonic solution at a pH between 7 and 7.5 at 35° C., more preferably between 85%-wt. and 93%-wt. In addition, the hydrogel should be free of any toxic or irritating extractables, sufficiently stable and sterilizable.

Suitable hydrogels for the cervical dilator include hydrogels with a network at least partly based on physical interactions rather than on covalent bonding. Examples of such hydrogels are hydrogels based on polyvinyl alcohol (PVA), as described, e.g., in the following US patents: U.S. Pat. Nos. 4,734,097, 4,663,358, 5,981,826, 6,231,605 and 7,332,117, each of which is incorporated herein by reference in its entirety.

Another suitable class of hydrogels for the cervical dilator are hydrophilic polyurethanes and polyureas (HPU). Examples of such hydrophilic polyurethanes and polyureas can be found in U.S. Pat. No. 5,688,855, which is incorporated herein by reference in its entirety.

While both PVA and HPU hydrogels have good mechanical properties in the hydrated state, they may lack ionic groups, such as sulpho-, sulphate or carboxyl groups, which provide the hydrogel with a Fixed Negative Charge Density (FNCD) that improves the swelling pressure.

Thus, the most preferred polymers for hydrogels for the cervical dilator are physically crosslinked acrylic hydrogels based on multi-block copolymers (MBC). For example, these "thermoplastic" hydrogels are based on hydrolyzed or aminolyzed polyacrylonitrile (PAN) and are described in several US patents, such as U.S. Pat. Nos. 4,943,618, 5,252,692, 6,593,451, 6,451,922, 6,232,406, 5,252,692, 4,420,589, 4,379,874, 4,369,294, 4,370,451, 4,337,327, 4,331,783, 4,107,121 and 3,948,870, each of which is incorporated herein by reference in its entirety.

These hydrogels based on hydrolyzed or aminolyzed PAN are known for their high mechanical strength (and their high resistance to fracture propagation and fatigue) even at a high water content. Their pendant nitrile groups are organized into sequences (or "blocks") that alternate with sequences of hydrophilic acrylic groups selected from acrylamide, N-substituted acryl amide, acrylamidine, N-substituted acryl amidine and acrylic acid and its salts. The sequences from monomer units with pendant nitrile groups separate themselves from the other polymer structures as crystalline domains with crystallinity typical for PAN that can be detected, e.g., by X-ray diffraction or by solid-state NMR. The crystalline domains form a 3D network that provides the hydrogel with high mechanical strength even at a high water content. Hydrophilic acrylate monomer units form the hydrophilic amorphous phase that absorbs aqueous liquids and expands as a consequence of the hydration. Particularly preferred are hydrogels with a high content of negatively charged pendant groups in amorphous domains, such as sulfo- or carboxylate groups in N-substituted amides and amidines, or carboxylates in the acrylic acid units. The concentration of the pendant negatively charged groups in the polymer is often expressed as Fixed Charge Density (FCD) in moles of charged groups per mole of monomer units. A high FCD is advantageous for osmotic pressure and swelling pressure generation, particularly at a high water content. The FCD in the MBC chains can be supplemented by charges from polyelectrolytes incorporated into the hydrogel structure in the form of a polymer blend or an interpenetrating network (IPN). The blend can be prepared, for example, by forming a dispersion of a polyelectrolyte in the MBC solution or its melt prior to the hydrogel formation. Such polyelectrolytes may be incorporated in their dry, powder form. Examples of suitable polyelectrolytes are polymers and copolymers of acrylic and methacrylic acid; poly(ethylene sulfonic acid); poly(phosphoric acid); poly(styrene sulfonic acid); poly(vinyl sulfuric acid); poly(vinylphosphonic acid); poly(maleic acid); poly(2-methacryloyloxyethane-1-sulfonic acid); poly(3-methacryloyloxypropane-1-sulfonic acid); poly(3-(vinyloxy)propane-1-sulfonic acid); poly(4-vinylphenyl sulfuric acid); and their respective salts, which can be formed by their neutralization prior to or after blending. Preferred salts are those with monovalent counter-cations such as sodium, potassium, lithium, ammonium or organic bases such $NR_4^+$ or $NR_3H^+$ (wherein R denotes alkyl or hydroxyalkyl substituents with one to four carbon atoms), pyridine, etc.

The xerogel stems in the form of a rod containing an osmotically active compound and optionally plasticizers are then cut to size, trimmed and equipped with suitable handles and guiding threads, as would be understood in the art. Preferably, the final cervical dilator product is then enclosed into a sterilization container and sterilized. The sterilization can be carried out, for example, by a gas, such as ethylene oxide, by ozone, by vapors of peracetic acid or by other means known to those of ordinary skill in the art. The preferred mode of sterilization is irradiation by ionizing rays, such as gamma rays, beta rays, or by accelerated electron beam. The irradiation is preferably carried out on a partly dehydrated xerogel that contains water in the concentration range from 3%-wt. to 25%-wt., and more preferably from 5% to 19%-wt.

EXAMPLES

Example 1

A hydrogel for the cervical dilator was prepared according to U.S. Pat. No. 6,232,406, which is incorporated herein by reference in its entirety. PAN of weight average molecular weight of 200,000 g/mol was dissolved in 55%-wt. NaSCN aqueous solution to form a 10%-wt. polymer solution. NaOH dissolved in 55%-wt. NaSCN aqueous solution was added at ambient temperature in an amount required for the PAN/NaOH mass ratio to be 1:10. Then, the solution was transferred into a jacketed tubular reactor, where it was heated to 70° C. for 60 hours. The resulting solution of the multi-block acrylic copolymer was cooled to 40° C. and transferred into a pressure vessel from where it was fed by a pressurized gas to a metering pump with a progressing cavity rotor. The solution was extruded through a cooled nozzle into a coagulation bath filled with NaSCN aqueous solution having an NaSCN concentration from 1 to 5%-wt. The coagulated hydrogel rod was washed until substantially all of the NaSCN was removed. The hydrogel was then immersed for 48 hours total into an excess of aqueous solution with different concentrations of NaCl (approximately 1%, 7.5%, 10%, 12.5% and 20% by weight), wherein the solutions were replaced with fresh salt solutions twice after 24-hour intervals to obtain an equilibrium NaCl distribution between the hydrogel and the liquid phase.

Sections of the hydrogel rods with different NaCl concentrations were stretched into a drying rack with a relative length extension of 25% and fixed with clamps. The rack was placed into a drying oven with airflow and dried at 125° C. for 24 hours. Then, the xerogel rods were cut into sections approximately 75 mm long, and each was equipped with a glued-on plastic handle on one side and ground to a rounded shape on the other. The xerogel was then stored in humid air to pick up about 15%-wt of moisture.

The concentration of NaCl in the hydrogel in equilibrium with the NaCl solution and in the final xerogel stem was established by extraction of NaCl into distilled water and argentometric titration of chlorides. The NaCl concentration in the hydrogel and in the final xerogel stem is shown in FIG. 1.

The cervical dilators with water-plasticized and NaCl-loaded cells were sealed into sterilization pouches and sterilized by gamma irradiation at the dose of 25 to 50 kGy. When compared with completely dried cervical dilators sterilized under the same conditions, the product sterilized in the water-plasticized state showed much lower discoloration and improved mechanical strength after swelling in buffered isotonic solution. The water-plasticized xerogel also demonstrated faster initial swelling and was resistant to fracture. The recommended water content of the cervical dilator is from 4 to 20%-wt, preferably from 8 to 15%-wt., based on the weight of the stem.

Sterile products combining the xerogel and salt of Example 1 provide accelerated cervical tissue ripening and cervical tissue expansion in comparison with similar hydrogel dilators containing no water-soluble salt.

Example 2

Hydrogels prepared according to Example 1 were soaked with 10%-wt. aqueous solutions of the following monomers:
1. sodium acrylate
2. methacryloyloxypropane-1-sulfonic acid
3. 4-vinylphenyl sulfuric acid
4. vinylphosphonic acid.

After equilibrium was reached in each solution, the monomer-soaked hydrogel rods were stretched on drying racks similarly as in Example 1, and dried at 80° C. for 18 hours. Although no initiator was used and drying was performed in the presence of air, all monomers polymerized and an interpenetrating network of a polyelectrolyte within the multiblock copolymer hydrogel was formed. When swelled in isotonic solution, no elution of the polyelectrolyte was observed, because it is apparently firmly anchored within the hydrogel structure.

Figure 2:
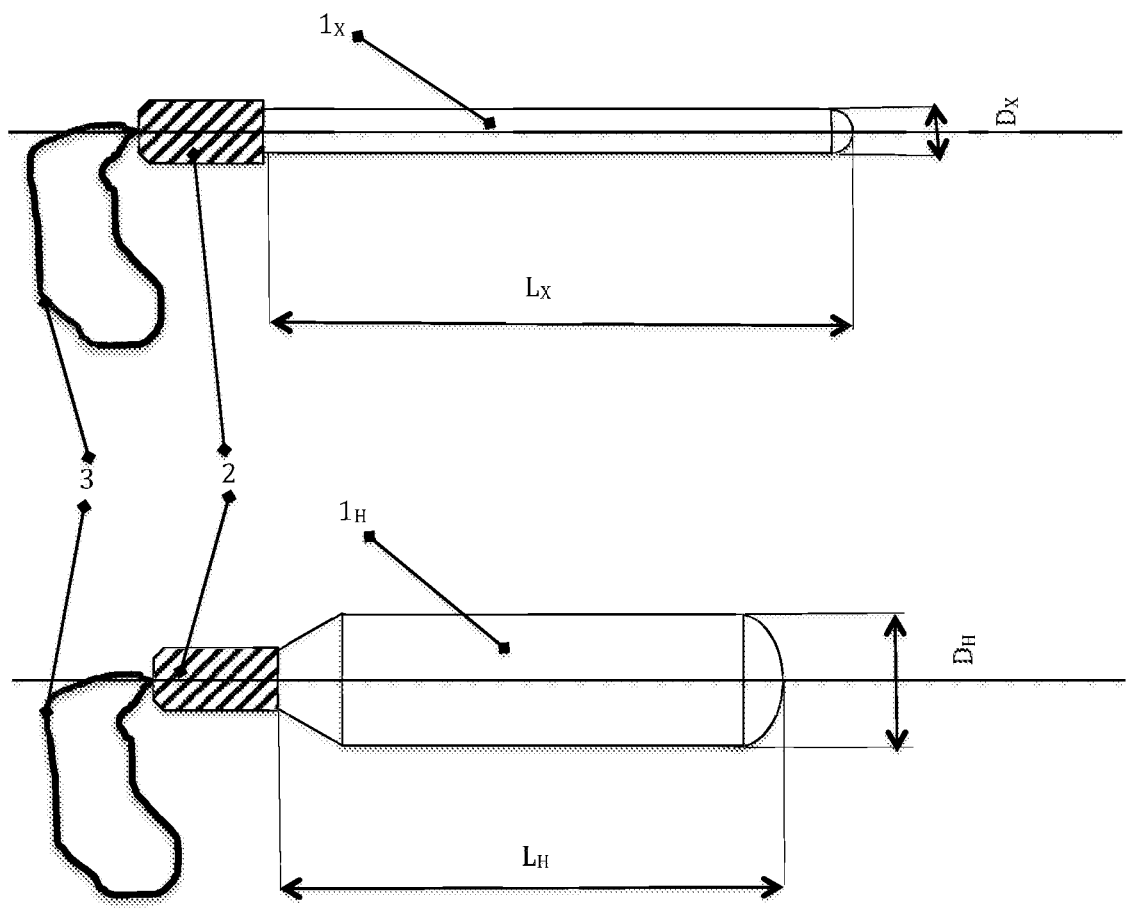
FIG. 2 shows a perspective view of a cervical dilator in a dehydrated state (in the top drawing) and in a hydrated state (in the bottom drawing).

The xerogel stems could then be equipped with glued-on plastic handles and sterilized by irradiation or by a gas. FIG. 2 shows a cervical dilator in a dehydrated state (top drawing) and in a hydrated state (bottom drawing). In FIG. 2: "$1_x$" denotes the anisotropically swellable xerogel stem in its original sterile state, fully or partly dehydrated; "$1_H$" denotes the hydrated hydrogel stem, fully hydrated in an isotonic solution at pH=7.0 to 7.5 at 35° C.; "2" denotes the plastic handle glued onto the stem; and "3" denotes the locator loop. In reference to FIG. 2, the xerogel stem length $L_X$ and diameter $D_X$ change to the hydrated hydrogel stem length $L_H$ and diameter $D_H$. Due to the anisotropic swelling, $(D_H/D_X) \gg (L_H/L_X)$. Preferably, $(D_H/D_X)$ is from 2 to 5, and more preferably, from 3 to 4. Preferably, $(L_H/L_X)$ is from 0.7 to 1.5, and more preferably, from 0.85 to 1.15. Also, the locator loop 3 may be a thread made from, for example, polyamide, polyolefin, polyester, polyurethane or cellulose.

Compared to the device from the salt-free hydrogel rods according to Example 1, the cervical dilator product of Example 2 shows increased anisotropic radial expansion with increased radial swelling pressure and swelling rate, as well as a faster ripening of the cervical tissue due to the stronger osmotic dehydration.

Example 3

The hydrogel interpenetrating network from Example 2 with the poly(methacryloyloxypropane-1-sulfonic acid) monomer was soaked with excess of aqueous solution containing 5%-wt. of sodium sulfate, 3%-wt. of 1,2-propyleneglycol and 1%-wt. of tri-ethanol amine. Then, it was dried under radial tension at 70° C. until the residual water content reached approximately 18%-wt. Then, the product was cut to size, trimmed, equipped with handles and sealed in the sterilization pouches as in previous examples. The cervical dilator device was sterilized by electron beam at 40 kGy. This cervical dilator device provides for a fast cervix ripening with strong radial expansion and the capability to be shaped prior to insertion to fit any particular geometry of cervical canal.

The foregoing examples and description should be taken as illustrating, rather than limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

All articles, references and patents cited herein are incorporated herein by reference in their entireties.

The invention claimed is:
1. A cervical dilator comprising:
a stem comprising a partly or fully dehydrated hydrogel comprising a water-insoluble osmotically active synthetic hydrophilic polymer capable of radial expansion due to absorption of water from a bodily fluid, causing a first osmotic dehydration; and
at least one second osmotically active compound, dispersed within the hydrogel, causing a second osmotic dehydration;
wherein:
the at least one second osmotically active compound is a polymeric electrolyte entrapped in the hydrogel network, wherein at least 50%-wt of the polymeric electrolyte remains entrapped within the hydrogel during a cervical expansion procedure;
the polymeric electrolyte forms an interpenetrating network with the water-insoluble osmotically active synthetic hydrophilic polymer forming the hydrogel, or the polymeric electrolyte is present in the form of discrete domains dispersed within the hydrogel;
the cervical dilator is configured to cause osmotic withdrawal of water from tissue using the first and second osmotic dehydrations;
the water-insoluble synthetic osmotically active hydrophilic polymer is selected from the group consisting of polyvinyl alcohol, polyurethane, polyurea, and acrylic copolymer comprising pendant nitrile and carboxylate groups; and
the at least one second osmotically active compound is selected from:
a water-soluble polymeric electrolyte, which is a polymer with pendant substituents selected from the group consisting of a carboxylate group, a salt of the carboxylate group, a sulfate group, a salt of the sulfate group, a phosphate group, a salt of the phosphate group, a sulfonic acid group, and a salt of the sulfonic acid group; or
a non-toxic water-soluble salt comprising a monovalent cation selected from the group consisting of sodium, potassium, lithium, an ammonium and an organic amine cation, and an anion selected from the group consisting of chloride, bromide, a sul- fate, a phosphate, a thiocyanate and an acetate anion, or a mixture of non-toxic water-soluble salts.

2. The cervical dilator according to claim 1, wherein the at least one second osmotically active compound is a polymeric electrolyte present in a concentration from 1%-wt to 60%-wt, preferably from 5%-wt to 40%-wt based on the dehydrated hydrogel stem.

3. The cervical dilator according to claim 2, wherein the polymeric electrolyte comprises a polymer with pendant substituents selected from the group consisting of a carboxylate group, a salt of the carboxylate group, a sulfate group, a salt of the sulfate group, a phosphate group, a salt of the phosphate group, a sulfonic acid group, and a salt of the sulfonic acid group.

4. The cervical dilator according to claim 1, wherein the polymeric electrolyte forms an interpenetrating network with the water-insoluble synthetic osmotically active hydrophilic polymer forming the hydrogel.

5. The cervical dilator according to claim 1, wherein the salt or salts are present in a concentration in a range from about 3%-wt. to 60%-wt., based on the weight of the hydrogel or, the salt or salts are present in a concentration in a range from about 7%-wt. to 45%-wt or, the salt or salts are present in a concentration in a range from about 9%-wt. to 35%-wt.

6. The cervical dilator according to claim 1, wherein the hydrogel contains from about 3%-wt. to 25%-wt. of a non-toxic plasticizer, based on the weight of the hydrogel, wherein preferably the plasticizer comprises at least one of the compounds selected from the group consisting of glycerol, glycerol monoacetate, glycerol diacetate, glycerol formate, glycolic acid, 1,2 propylene glycol, dimethylsulfoxide (DMSO) and water and optionally, wherein the hydrogel contains from about 5%-wt. to 22%-wt. of water.

7. The cervical dilator according to claim 1, wherein the partly or fully dehydrated hydrogel stem is capable of radial expansion by more than 200% of its dehydrated diameter while its axial dimension change is from +25% to −25% of its dehydrated length under the same conditions.

8. The cervical dilator according to claim 1, wherein the hydrogel comprises an acrylic copolymer comprising pendant nitrile and carboxylate groups, wherein the copolymer is optionally a product of partial hydrolysis and/or aminolysis of polyacrylonitrile (PAN) and optionally wherein the pendant nitrile groups are organized into crystalline domains detectable by X-ray diffraction.

9. A method of manufacturing the cervical dilator according to claim 1, the method comprising:
providing a hydrogel in a partly or fully dehydrated state;
axially stretching the hydrogel at a temperature above the glass transition temperature of the water-insoluble synthetic hydrophilic polymer, thereby producing the stem comprising the partly or fully dehydrated hydrogel, and achieving the capability of radial expansion; and
subsequently cooling the stem comprising the partly or fully dehydrated hydrogel under the axial stress to an ambient temperature.

10. A method of manufacturing the cervical dilator according to claim 1, the method comprising:
providing a hydrogel in a hydrated state;
axially stretching the hydrogel and maintaining a predetermined length of the hydrogel while drying the hydrogel, thereby producing the stem comprising the partly or fully dehydrated hydrogel, and achieving the capability of radial expansion.

11. The method of claim 9, wherein the hydrogel comprises an acrylic copolymer comprising pendant nitrile and carboxylate groups, wherein the copolymer is a product of a partial hydrolysis or aminolysis of polyacrylonitrile (PAN), and wherein the partial hydrolysis or aminolysis is achieved by reacting the PAN dissolved in a concentrated solution of sodium thiocyanate in the presence of a hydroxide of an alkali metal, preferably sodium hydroxide, to yield a viscous solution of the partly hydrolyzed or aminolyzed polyacrylonitrile copolymer, wherein optionally the partial hydrolysis or aminolysis is achieved at a temperature in the range from 30° C. to 100° C., preferably from 50° C. to 85° C. and preferably wherein the viscous solution of the partly hydrolyzed or aminolyzed polyacrylonitrile copolymer is converted into the hydrogel by coagulating the solution with an aqueous liquid followed by a full or partial extraction of the thiocyanate solvent and by a subsequent drying step.

12. The method of claim 10, wherein the hydrogel comprises an acrylic copolymer comprising pendant nitrile and carboxylate groups, wherein the copolymer is a product of a partial hydrolysis or aminolysis of polyacrylonitrile (PAN), and wherein the partial hydrolysis or aminolysis is achieved by reacting the PAN dissolved in a concentrated solution of sodium thiocyanate in the presence of a hydroxide of an alkali metal, preferably sodium hydroxide, to yield a viscous solution of the partly hydrolyzed or aminolyzed polyacrylonitrile copolymer, wherein optionally the partial hydrolysis or aminolysis is achieved at a temperature in the range from 30° C. to 100° C., preferably from 50° C. to 85° C. and preferably wherein the viscous solution of the partly hydrolyzed or aminolyzed polyacrylonitrile copolymer is converted into the hydrogel by coagulating the solution with an aqueous liquid followed by a full or partial extraction of the thiocyanate solvent and by a subsequent drying step.

13. The method of claim 9, wherein the at least one osmotically active compound includes a non-toxic water-soluble salt or a mixture of non-toxic water-soluble salts, wherein the hydrogel contains from about 3%-wt. to 25%-wt. of a non-toxic plasticizer, and wherein the hydrogel is kept in contact with an aqueous solution of the at least one osmotically active compound and/or a precursor of the at least one osmotically active compound and/or the plasticizer prior to a drying step for a time necessary for the at least one osmotically active compound to penetrate into the hydrogel in a sufficient concentration.

14. The method of claim 10, wherein the at least one osmotically active compound includes a non-toxic water-soluble salt or a mixture of non-toxic water-soluble salts, wherein the hydrogel contains from about 3%-wt. to 25%-wt. of a non-toxic plasticizer, and wherein the hydrogel is kept in contact with an aqueous solution of the at least one osmotically active compound and/or a precursor of the at least one osmotically active compound and/or the plasticizer prior to a drying step for a time necessary for the at least one osmotically active compound to penetrate into the hydrogel in a sufficient concentration.

15. The method of claim 9, further comprising sterilizing the cervical dilator within a container impermeable to water and water vapors by exposing it to an ionizing radiation and wherein optionally
a) the ionizing radiation is gamma radiation or
b) is an electron beam (or beta) radiation.

16. The method of claim 10, further comprising sterilizing the cervical dilator within a container impermeable to water and water vapors by exposing it to an ionizing radiation and wherein optionally
   a) the ionizing radiation is gamma radiation or
   b) is an electron beam (or beta) radiation.

17. The cervical dilator according to claim 1, wherein the polymeric electrolyte is present in the form of discrete domains dispersed within the hydrogel.

* * * * *